(12) United States Patent
Chapman et al.

(10) Patent No.: US 12,089,729 B2
(45) Date of Patent: *Sep. 17, 2024

(54) MULTIFUNCTIONAL DENTAL APPLIANCE AND TOOTHBRUSH CLEANER

(71) Applicant: SDC U.S. SmilePay SPV, Nashville, TN (US)

(72) Inventors: Josh Chapman, Nashville, TN (US); Brittany Lacey, Nashville, TN (US)

(73) Assignee: SDC U.S. SmilePay SPV, New York, NY (US)

( * ) Notice: Subject to any disclaimer, the term of this patent is extended or adjusted under 35 U.S.C. 154(b) by 273 days.

This patent is subject to a terminal disclaimer.

(21) Appl. No.: 17/239,781

(22) Filed: Apr. 26, 2021

(65) Prior Publication Data

US 2021/0235861 A1 Aug. 5, 2021

Related U.S. Application Data

(63) Continuation of application No. 16/540,939, filed on Aug. 14, 2019, now Pat. No. 10,986,917.

(51) Int. Cl.
*A46B 17/06* (2006.01)
*A61L 2/10* (2006.01)

(52) U.S. Cl.
CPC ............. *A46B 17/065* (2013.01); *A61L 2/10* (2013.01); *A46B 2200/1066* (2013.01); *A61L 2202/122* (2013.01)

(58) Field of Classification Search
CPC .... A61L 2/10; A61L 2202/122; A46B 17/065
See application file for complete search history.

(56) References Cited

U.S. PATENT DOCUMENTS

| | | | | |
|---|---|---|---|---|
| 4,816,648 A | * | 3/1989 | Dusbabek | H05B 3/14 |
| | | | | 219/505 |
| 4,950,902 A | | 8/1990 | Ritter | |
| 5,487,877 A | * | 1/1996 | Choi | A47K 5/00 |
| | | | | 250/455.11 |

(Continued)

FOREIGN PATENT DOCUMENTS

| | | |
|---|---|---|
| CN | 201012181 Y | 1/2008 |
| CN | 201127736 Y | 10/2008 |

(Continued)

*Primary Examiner* — Kevin Joyner
(74) *Attorney, Agent, or Firm* — Foley & Lardner LLP

(57) ABSTRACT

A cleaning device includes a body, a cover, a germicidal lamp, and a vibration mechanism. The body includes a cavity configured receive a fluid, a first dental appliance, and a first portion of a second dental appliance. The cover is coupled to the body and configured to selectively move between an open position and a closed position. The cover includes two holes that can each retain the second dental appliance so the first portion of the second dental appliance is positioned within the cavity and a second portion of the second dental appliance is positioned external to the cavity and the cover. The germicidal lamp is coupled to the cover and configured to provide a sanitizing light to the first dental appliance and the first portion of the second dental appliance positioned within the cavity. The vibration mechanism is configured to vibrate the body and the dental appliances.

17 Claims, 8 Drawing Sheets

(56) References Cited

U.S. PATENT DOCUMENTS

| | | |
|---|---|---|
| 6,171,548 B1 | 1/2001 | Rose et al. |
| 7,179,436 B2 | 2/2007 | Paskal et al. |
| 7,213,603 B2 | 5/2007 | Pinsky |
| 7,511,283 B2 | 3/2009 | Chor |
| 7,771,540 B2 | 8/2010 | Schwartz |
| 7,798,159 B2 | 9/2010 | Palfy et al. |
| 7,838,846 B2 | 11/2010 | Pinsky |
| 8,002,897 B2 | 8/2011 | Palfy et al. |
| 9,888,691 B2 | 2/2018 | Karandikar et al. |
| 2007/0057197 A1 | 3/2007 | Chor |
| 2007/0080081 A1 | 4/2007 | Chang |
| 2010/0326484 A1 | 12/2010 | Wu |
| 2014/0319375 A1 | 10/2014 | Nelson et al. |
| 2016/0000953 A1* | 1/2016 | Bettles ................ A61L 2/10 |
| | | 250/455.11 |
| 2019/0313785 A1 | 10/2019 | Jimenez et al. |

FOREIGN PATENT DOCUMENTS

| | | |
|---|---|---|
| CN | 101318024 A | 12/2008 |
| CN | 101366956 B | 2/2009 |
| CN | 201500654 U | 6/2010 |
| CN | 201759878 U | 3/2011 |
| CN | 102068708 A | 5/2011 |
| CN | 105816892 A | 8/2016 |
| CN | 108746058 A | 11/2018 |
| DE | 10061927 C2 | 6/2002 |
| DE | 10 2005 007 617 B3 | 9/2006 |
| GB | 1 416 979 A | 12/1975 |
| KR | 100770628 B1 | 10/2007 |
| KR | 100951612 B1 | 4/2010 |
| KR | 20100052073 A | 5/2010 |
| KR | 101586301 B1 | 1/2016 |

\* cited by examiner

MULTIFUNCTIONAL DENTAL APPLIANCE AND TOOTHBRUSH CLEANER

CROSS-REFERENCE TO RELATED APPLICATIONS

This application is a continuation of U.S. patent application Ser. No. 16/540,939, filed Aug. 14, 2019, which is incorporated herein by reference in its entirety.

BACKGROUND

Dental appliances become dirty and unsanitary after normal use. For example, dental aligners for repositioning teeth and retainers for maintaining the position of repositioned teeth become dirty and unsanitary by being worn in a user's mouth, and toothbrushes become dirty and unsanitary after being used to brush teeth. Because normal use of these products result in development of bacteria, it is necessary for a user to clean and sanitize such products to minimize bacteria growth and promote oral health.

Users of dental appliances typically have to clean the dental appliance after each use. Some users clean their appliances by simply splashing the appliance with water. Others soak their dental appliances in a solution. Often, a user must clean each dental appliance separately, which can be cumbersome.

SUMMARY

One embodiment relates to a cleaning device. The cleaning device includes a body including a cavity configured to receive a fluid, a first dental appliance, and a first portion of a second dental appliance. The cleaning device includes a cover coupled to the body and configured to selectively move between an open position and a closed position. The cover includes two holes, each hole configured to retain the second dental appliance such that the first portion of the second dental appliance is positioned within the cavity and a second portion of the second dental appliance is positioned in an area external to the cavity and the cover. The cleaning device includes a germicidal lamp coupled to the cover and configured to provide a sanitizing light to the first dental appliance and the first portion of the second dental appliance positioned within the cavity. The cleaning device includes a vibration mechanism configured to vibrate the body, and the dental appliances.

Another embodiment relates to a cleaning device. The cleaning device includes a body including a cavity configured to receive a fluid, a first dental appliance, and a first portion of a second dental appliance. The cleaning device includes a cover coupled to the body and configured to selectively move between an open position and a closed position. The cover includes two holes opposite one another, each hole configured to retain the second dental appliance such that the first portion of the second dental appliance is positioned within the cavity and a second portion of the second dental appliance is positioned in an area external to the cavity and the cover. The cleaning device includes a germicidal lamp configured to provide a sanitizing light the first dental appliance and the first portion of the second dental appliance positioned within the cavity. The cleaning device includes a vibration mechanism configured to vibrate the body and the dental appliances.

Another embodiment relates to a cleaning device. The cleaning device includes a body including a cavity configured to receive a fluid and a plurality of dental appliances. The cleaning device includes a cover coupled to the body and configured to selectively move between an open position and a closed position. The cover includes two holes opposite one another, each hole configured to retain a portion of a first dental appliance of the plurality of dental appliances and a portion of a second dental appliance of the plurality of dental appliances such that the portions of the dental appliances are angled toward a center of the cavity, wherein the first dental appliance and the second dental appliance are configured to brush teeth of a user. The cleaning device includes a germicidal lamp configured to provide a sanitizing light to the portions of the dental appliances that are angled toward the center of the cavity. The cleaning device includes a vibration mechanism configured to vibrate the body and the dental appliances.

DETAILED DESCRIPTION

Figure 1:
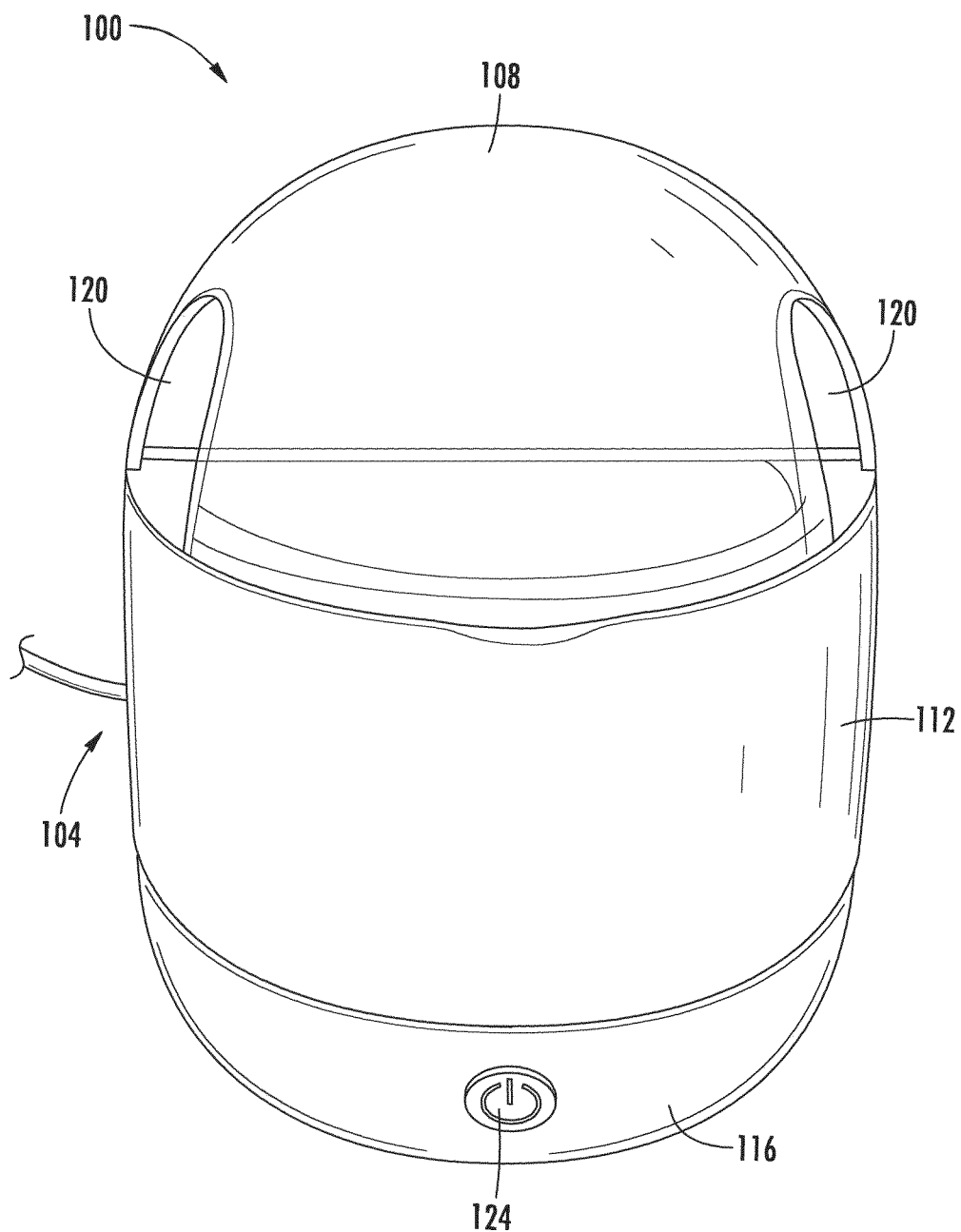
FIG. 1 is a perspective view of a cleaning device for a dental appliance in a closed configuration, according to some embodiments.

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

Referring generally to the figures, described herein is a cleaning device for cleaning at least one dental appliance. As used herein, dental appliance 204 refers to anything that a person may insert or wear within their mouth more than one time, including any oral products such as dental aligners, retainers, dentures, mouth guards, whitening trays, toothbrushes, flossing devices, dental picks, and tongue scrapers. The cleaning device includes a body, a cover, a vibration mechanism, and a germicidal lamp. The body may be defined by a cavity, an exterior base, and an exterior wall having a circular shape surrounding the exterior base. The cavity may be bounded by an interior base and an interior wall having a circular shape surrounding the interior base. The cavity configured to receive a fluid and the dental appliance. The cover includes at least one hole that is configured to receive at least a portion of the dental appliance. In some embodiments, the hole is a pair of opposed holes. The germicidal lamp may be coupled to the underside of the cover and configured to provide a sterilization light or a sanitizing light to the cavity. The vibration mechanism is configured to vibrate the body. In some embodiments, the cleaning device includes a removable tray configured to fit inside the cavity and support the dental appliance.

In operation, the cavity receives a fluid and a dental appliance from a user. In some embodiments, the dental appliance is received through the hole in the cover. In further embodiments, the dental appliance is received when the cover is in the open position. In other embodiments, the dental appliance is received using the removable tray. In other words, the user places the dental appliance on top of the tray and the removable tray is placed inside the cavity when the cover is in the open position. In additional embodiments, a plurality of dental appliance are received. For example, one dental appliance is received when the cover is in the open positon and another is received through the hole in the cover. Next, the user actuates the cleaning device, activating (e.g., powering) both the germicidal lamp and the vibration mechanism at the same time. When activated, the germicidal lamp provides sterilization light or sanitizing light to the cavity and the vibration mechanism vibrates the body. In some embodiments, the cavity further includes silver that contacts the dental appliances.

In some embodiments, if the user actuates the cleaning device a second time, the germicidal lamp is deactivated but the vibration mechanism is still activated. If the user actuates the cleaning device a third time, the germicidal lamp is activated and the vibration mechanism is deactivated. Finally, if the user actuates the cleaning device a fourth time, the germicidal lamp is deactivated. In further embodiments, if five minutes passes between actuation, both the vibration mechanism and the germicidal lamp are deactivated. Various other embodiments and advantages will become apparent according to the description which follows.

Figure 2:
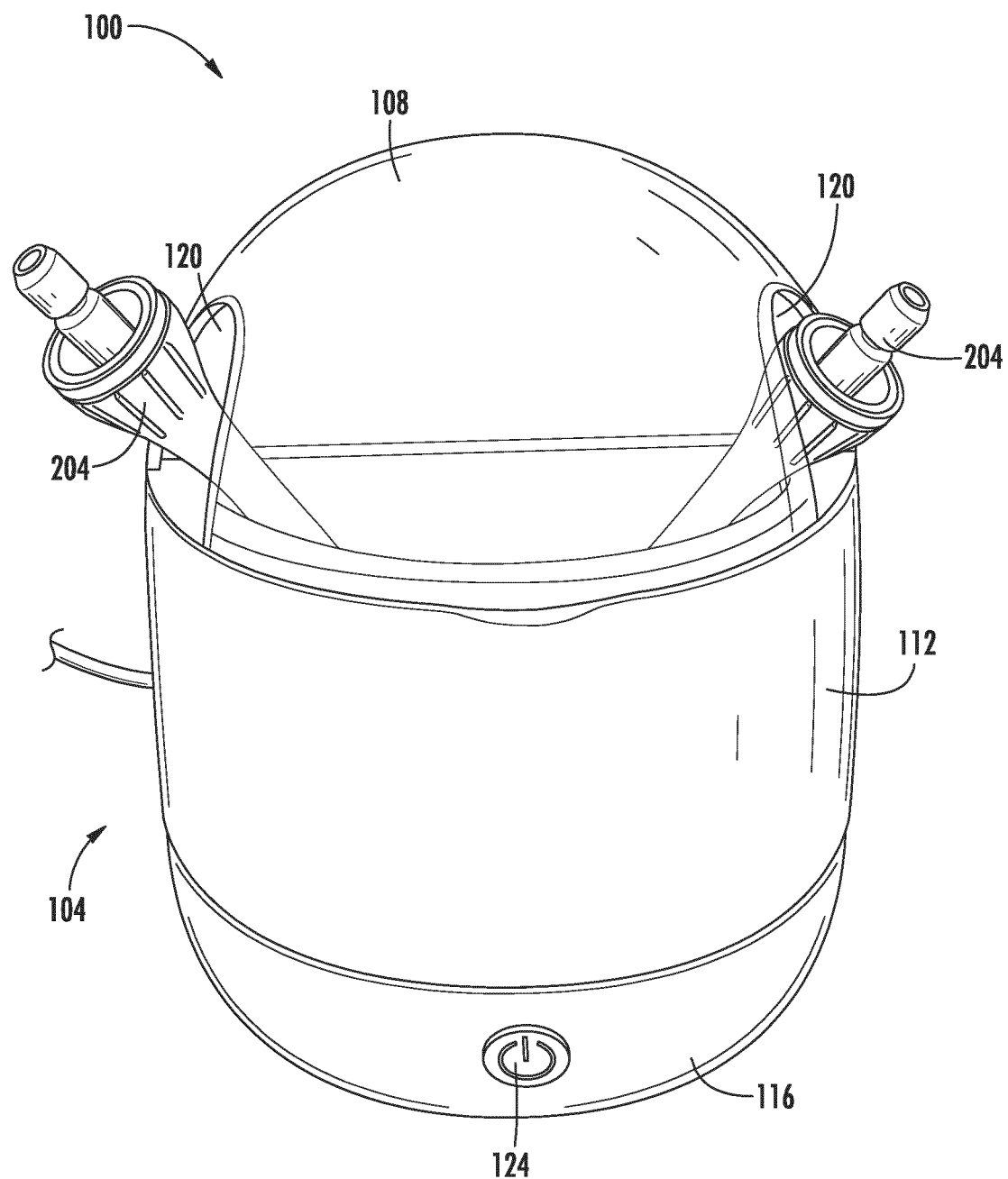
FIG. 2 is a perspective view of the cleaning device of FIG. 1 in the closed configuration with a plurality of dental appliances inserted therein, according to some embodiments.
Figure 3:
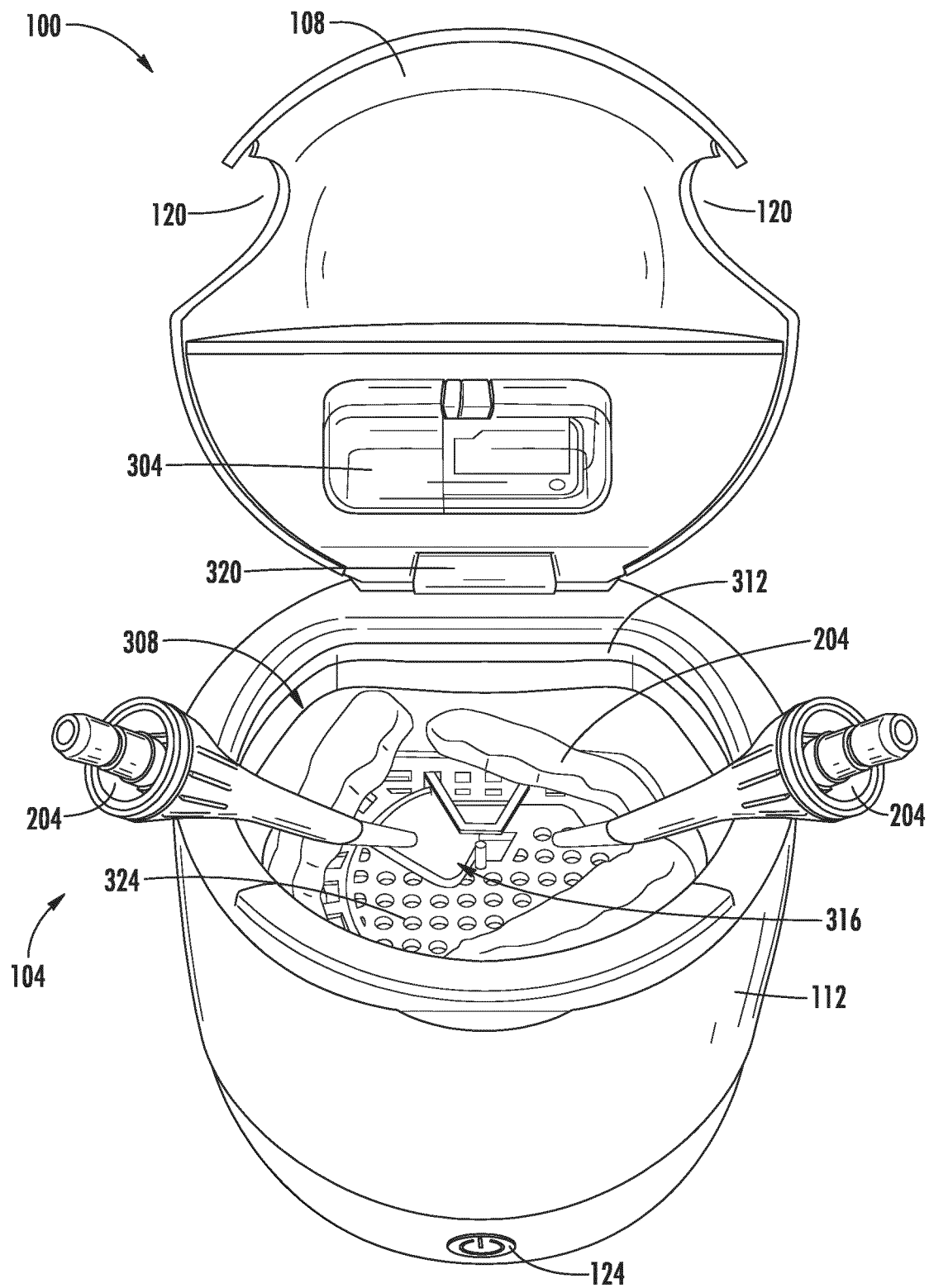
FIG. 3 is a perspective view of the cleaning device of FIG. 1 in an open configuration with a plurality of dental appliances inserted therein, according to some embodiments.
Figure 4:
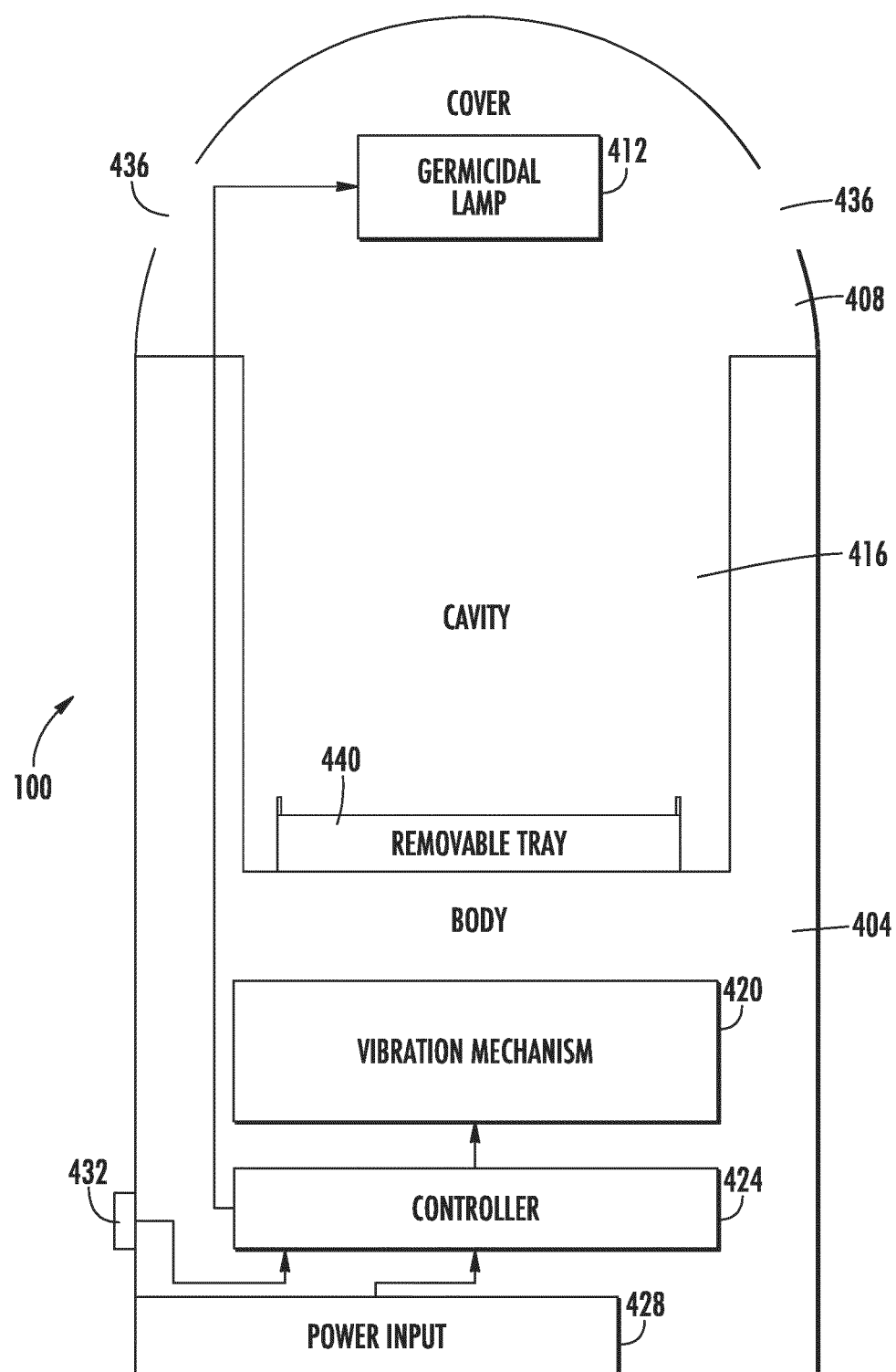
FIG. 4 is a block diagram of the cleaning device of FIG. 1, according to some embodiments.
Figure 5:
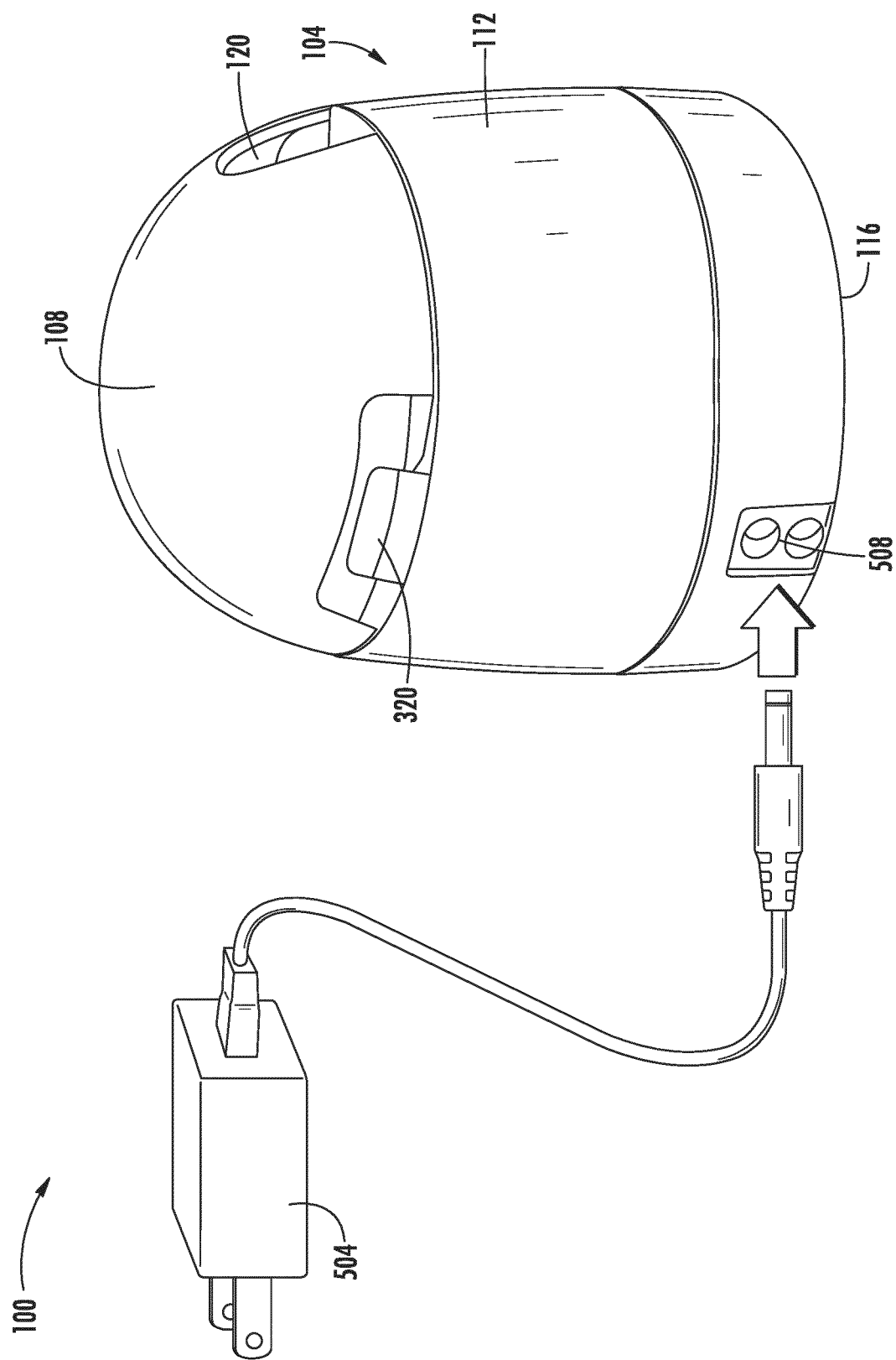
FIG. 5 is a rear perspective view of the cleaning device of FIG. 1 in the closed configuration with a power supply, according to some embodiments.
Figure 6:
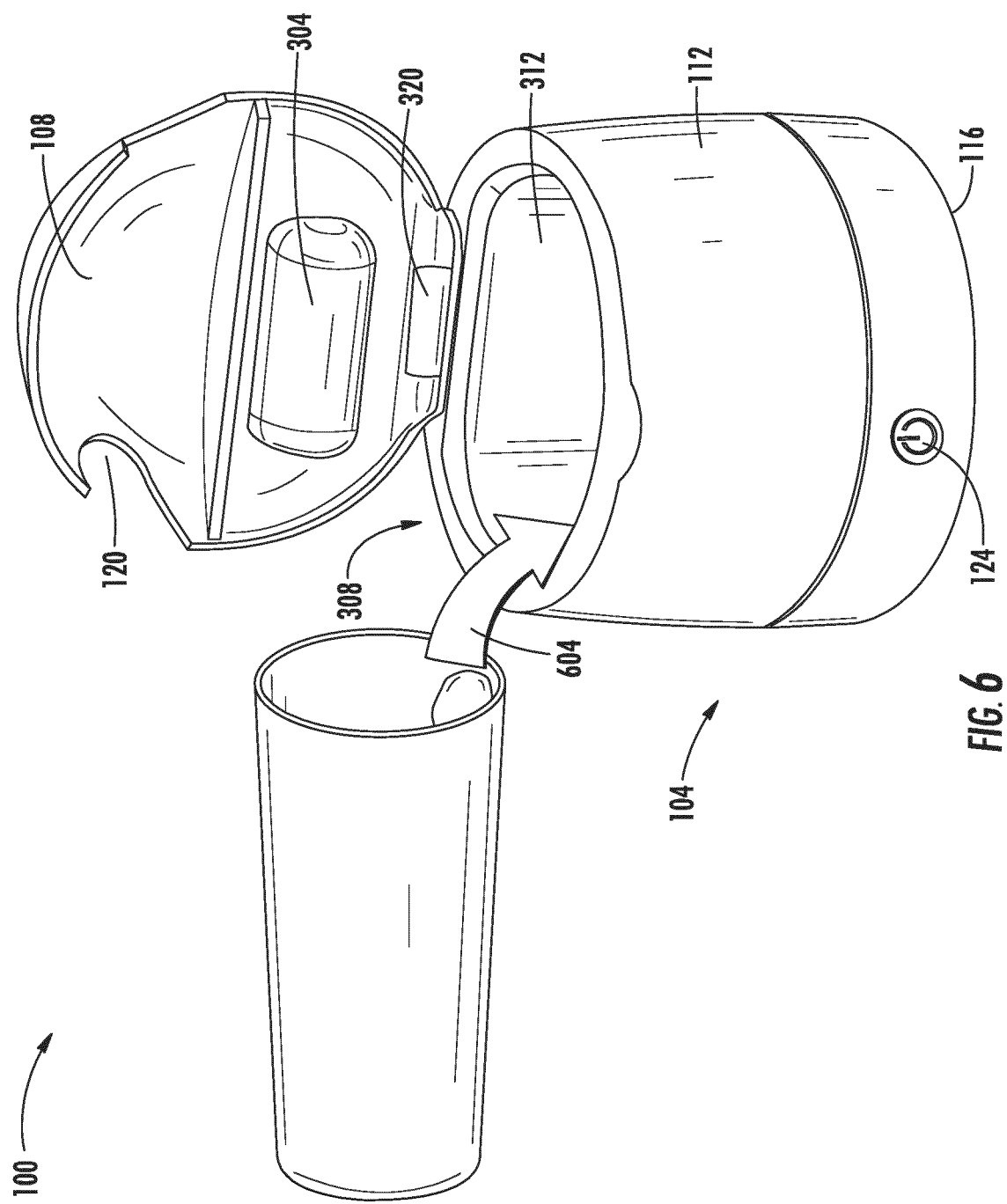
FIG. 6 is a front view of the cleaning device of FIG. 1 in the open configuration receiving a fluid, according to some embodiments.
Figure 7:
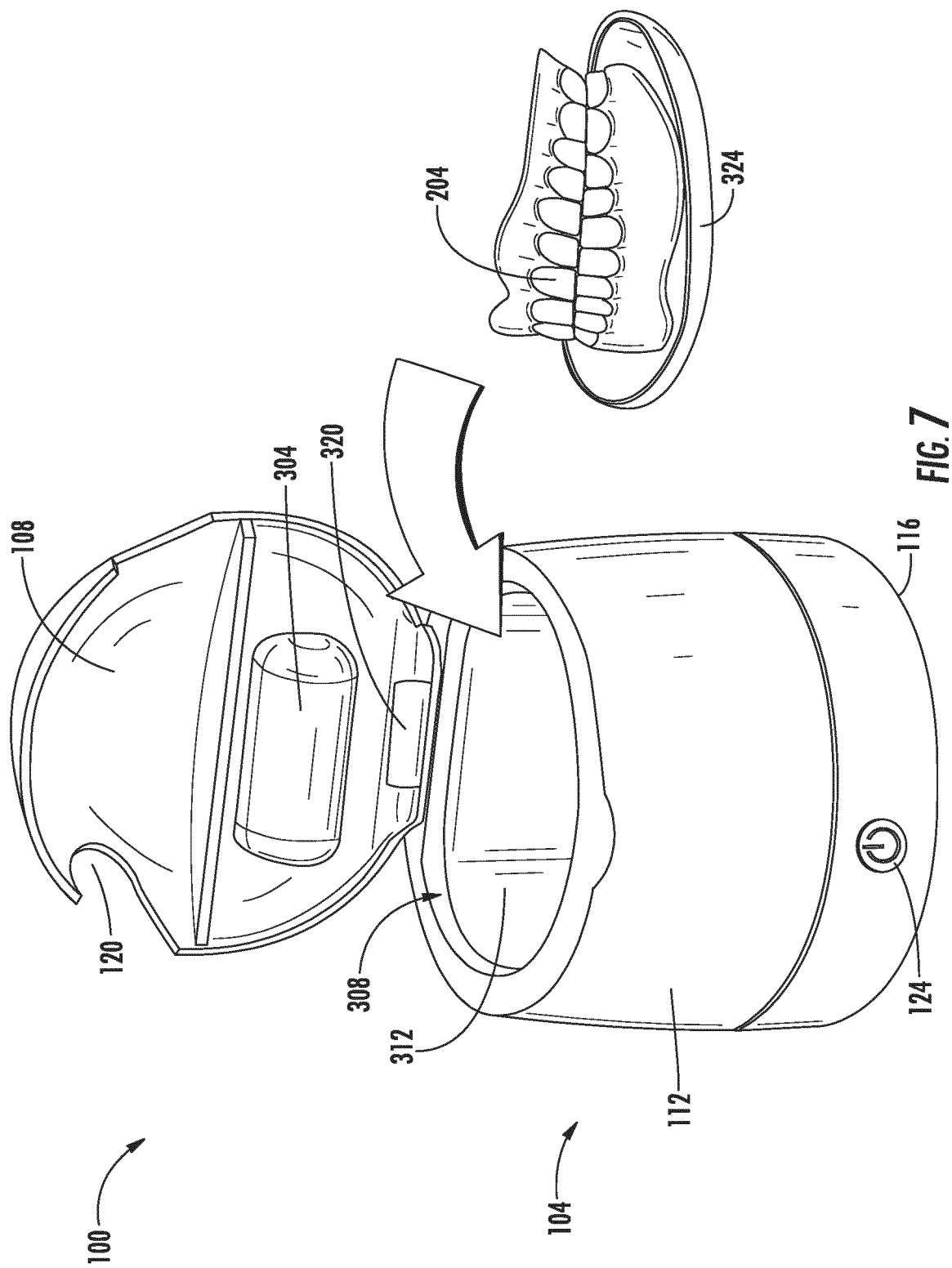
FIG. 7 is a front view of the cleaning device of FIG. 1 in the open configuration receiving a removable tray and a dental appliance, according to some embodiments.

Referring now to FIGS. 1-7, various views of a cleaning device 100 are shown. Specifically, FIG. 1 is a perspective view of the cleaning device 100 in a closed configuration, FIG. 2 is a perspective view of the cleaning device 100 with a plurality of dental appliances 204 in the closed configuration, FIG. 3 is a top view of the cleaning device 100 with the plurality of dental appliances 204 in an open configuration, FIG. 4 is a block diagram of the cleaning device 100 in a closed configuration, FIG. 5 is a rear view of the cleaning device 100 with a power supply 504 in the closed configuration, FIG. 6 is a front view of the cleaning device 100 receiving a fluid 604 in the open configuration, and FIG. 7 is a front view of the cleaning device 100 receiving a removable tray 324 and a dental appliance 204 in the open configuration, according to illustrative embodiments. As best shown in FIG. 3, the cleaning device 100 is shown to include a body 104, a cover 108, and a germicidal lamp 304. The body 104 may include an exterior wall 112 and an exterior base 116. The exterior wall 112 may surround the exterior base 116 (e.g., along a perimeter of the exterior base 116). The body 104 may further include a cavity 308. The cavity 308 may be bound by an interior wall 312 and an interior base 316. The interior wall 312 may surround the interior base 316 (e.g., along a perimeter of the interior base 316). The body 104 may additionally include a push button 124. Push button 124 may be configured to receive a force from the user, and in turn, provide a signal indicative that the push button 124 was pressed. In some embodiments, the push button 124 is communicably coupled to a controller such as controller 424 shown in FIG. 4. In the same embodiment, the push button 124 may be configured to send a signal to the controller when the user presses the push button 124.

The cover 108, exterior wall 112, and exterior base 116, may be constructed of various materials, such as various types of plastics, metals, resins, composites, quartz glass etc. In some embodiments, the cover 108 is made of quartz glass and the exterior wall 112 and the exterior base 116 are made of a different material. In some embodiments, the cover 108 is constructed of a material that is light absorbent, such as a dark (e.g., black, brown, grey) polycarbonate, dark high-density polyethylene (HDPE), or various other dark polymer materials. The cavity 308 may be designed or implemented to hold a fluid 604 and at least one dental appliance 204. For instance, the interior wall 312 and the interior base 316 may be made of a material, such as stainless steel, that is commonly used to hold fluids, such as water, but resistant to oxidation. Further, the cavity 308 may have a diameter at least as wide as an average person's mouth, an above average person's mouth, etc. The cavity 308 may thus be sized to hold and retain various embodiments of dental appliances 204, and specifically dental appliances 204 that may be worn in a user's mouth (e.g., on the user's teeth in the case of dental aligners). In some embodiments, the interior base 316 and the interior wall 312 may be coated with silver. The silver may contact a dental appliance 204 inside cavity 308. As silver has antibacterial properties, a silver coating further cleans the dental appliance 204 and helps eliminate bacteria in the liquid 604.

The dental appliance 204 includes any device, component, or appliance configured to be used inside of a user's mouth. This includes devices worn on a user's teeth in accordance with dental or orthodontic treatment. As one example, the dental appliance 204 may be dental aligners (shown in FIG. 3) configured to reposition one or more teeth of the user in accordance with a treatment plan (e.g., a series of dental aligners, each configured to incrementally move the user's teeth from a starting position to an ending position). As another example, the dental appliance 204 may be a retainer configured to be worn for maintaining a position of a user's teeth following orthodontic treatment, such as orthodontic treatment by way of dental aligners. As yet another example, the dental appliance 204 may be whitening trays configured to be worn for whitening the user's teeth. In another example, the dental appliance 204 can be a mouth guard for protecting the teeth of the user. In yet another example, the dental appliance 204 may be a pair of dentures (shown in FIG. 7), configured to look like real teeth when worn in a user's mouth. The dentures may be a full or partial set of dentures. As another example, the dental appliance 204 may be a plastic toothbrush used to clean a user's teeth. In another example, the dental appliance 204 may be the removable head of an electric toothbrush (shown in FIG. 1 and FIG. 3). The removable head may be fully detached from the body of the electric toothbrush, or it may still be attached to the body of the electric toothbrush. In a final example, the dental appliance 204 may be a dental instrument designed for use in a dental office such as a mirror, a probe, a dental forceps, a curette, etc. In some embodiments, the cleaning device is further configured receive and clean jewelry. The jewelry may be made of a variety of materials such as precious metals (e.g., gold, silver, copper, platinum, etc.), metal alloys, or jewels (e.g., diamonds, sapphire, emeralds, etc.).

In further embodiments, the dental appliance 204 may be a plurality of dental appliances 204. The dental appliance 204 may be a combination of one or more of the devices described above. The cleaning device 100 can receive and clean a plurality of dental appliances 204 at the same time, such as a toothbrush and a set of dental aligners, a dental aligner and two toothbrushes, and so on.

As best shown in FIG. 6, the cavity 308 is configured to receive a fluid 604. The fluid 604 may be any fluid. In some embodiments, the fluid 604 is a fluid with sanitizing properties used to sanitize dental appliance 204. For example, the fluid 604 may be water, hydrogen peroxide, sodium hypochlorite, chlorine dioxide, sodium dichloroisocyanurate, or chloramine-T. In some embodiments, the fluid may be salt water. In some embodiments, the fluid may be hot water (e.g., above 100° F.). In some embodiments, the fluid may be water that receives a chemical tablet. The chemical tablet may include silver, sodium bicarbonate, sodium carbonate, sorbitol, potassium monospersulfate, sodium perborate monohydrate, ethylenediaminetraacetic acid, polyethylene glycol, sodium benzoate, and sodium lauryl sulfoacetate. The chemical tablet may be configured to dissolve in water and sanitize dental appliances 204. In some embodiments, the chemical tablet may be configured to sanitize jewelry.

In some embodiments, the cleaning device 100 includes a removable tray 324. The removable tray 324 is configured to receive and support a dental appliance 204. The removable tray 324 may include a handle configured to allow a user to pick up and move removable tray 324. For example, a user may place a dental appliance 204 on the removable tray 324, grab the handle of the tray 324, and place it in the cavity 308. The removable tray 324 may further include a plurality of small holes configured to allow a fluid to permeate the removable tray 324. Therefore, once the removable tray 324 is in the cavity 308, the fluid 604 is allowed to permeate the removable tray 324 and contact the dental appliance 204 supported by removable tray 324. In some embodiments, the removable tray 324 is designed to absorb a minimal amount of light. For this reason, the removable tray 324 may be the color white. The removable tray 324 may be constructed of various materials such as, various types of plastics, metals, resins, composites, etc.

As can be best seen in FIG. 3, the cleaning device 100 is shown to include a cover 108 and a body 104. The cover 108 is configured to selectively move between a closed position (shown in FIG. 1) and an open position (shown in FIG. 3). When the cover 108 is in the open position, the cover 104 permits access to the cavity 308 and the contents thereof. The cover 108 is pivotably coupled to the body 104. The cover 108 is coupled to the body 104 via a hinge 320. In some embodiments, the cover 108 pivots approximately 90° relative to the body 104 to expose the cavity 308. The hinge 320 may be configured to provide a greater or lesser range of motion of the cover 108 relative to the body 104. For example, the cover 108 can pivot greater than 90° or less than 90° relative to the body 104.

As can be seen in FIG. 1-FIG. 3 and FIG. 6-FIG. 7, the cover 108 includes a pair of opposing holes 120. The holes 120 are located on opposite sides of the cover 108 and configured to, in some cases, receive at least a part of the dental appliance 204. The holes 120 may be configured to allow access to the cavity 308 and the contents thereof. The holes 120 can be located on opposite sides of the lid, but not diametrically opposite. In some embodiments, the holes 120 may be diametrically opposite. In some embodiments, the holes 120 are opposed as to keep a symmetric appearance on the cover 108. The holes 120 may have a half circle shape. The holes 120 may be defined by the cover 108 and part of the body 104 such that a dental appliance 204 inserted into one of the holes partially interfaces with the body 104. As stated above, the holes 120 are configured to hold at least part of a dental appliance 204. For example, the holes 120 may be designed or implemented to receive at least part of a toothbrush (e.g., with an end that is not being cleaned protruding from the cleaning device 100). In some embodiments, holes 120 may be designed or implemented to receive the neck of a toothbrush. In other words, the diameter of the holes 120 may be at least as large as the diameter of the average toothbrush, multiple times larger than the diameter of the average toothbrush (e.g., three to six times larger), etc. In some embodiments, the holes 120 may be located in positions other than those shown in FIG. 1-FIG. 3 and FIG. 6-FIG. 7. In some embodiments, the cleaning device 100 includes only one hole 120, two holes 102, three holes 120, four holes 120, five holes 120, or more than five holes 120. The holes 120 may be located anywhere on the cover 108. For example, the holes 120 may be located on opposite sides of the cover 108 such that the part of the dental appliance 204 (e.g. a tooth brush) to be cleaned is located underneath the sterilization light or sanitizing light. In other words, the holes 120 may be located on opposite sides and angled in such a way (e.g. angled within the cover 108 towards the center of the cavity 308) that when the dental appliance 204 is inserted into the holes 120, it naturally positions towards the center of the cavity 308 (e.g., to ensure the dental appliance 204 is directly underneath the light of the germicidal lamp 304). In some embodiments, the holes 120 are located on both sides of the germicidal lamp 304, such that an axis drawn between a center point of each hole 120 intersects with the germicidal lamp 304. In further embodiments, the holes 120 are located on both sides of the light and slightly forward of the germicidal lamp 304, such that an axis drawn between a center point of each hole 120 would be offset from the germicidal lamp 304 (e.g., offset by 0.1-3.0 inches, by 0.5-2.5 inches, by 1.0-2.0 inches, etc.).

Because the cover 108 includes a pair of opposing holes 120 and is configured to selectively move between an open position and a closed position, the cleaning device 100 has a distinct advantage in that it can be used on all forms of dental appliances. Because toothbrushes, aligners, retainers, whitening trays, dentures, and dental instruments have different shapes and sizes, it is difficult to create a device that can receive and clean all of the different types of dental appliances. The cleaning device 100 solves this problem through use of the cover 108 because cover 108 allows the user to access the cavity 308 through either the holes 120 or through selectively moving the cover 108 to the open position. This allows cleaning device 100 to clean many different dental appliances that a user may want to clean at a single time.

Referring to FIG. 3, the cleaning device 100 is shown to include the germicidal lamp 304. Germicidal lamp 304 is configured to provide a sterilization light and/or sanitizing light to the cavity 308. In some embodiments, the germicidal lamp is further configured to provide sanitization light to the dental appliances 204 located within the cavity 308. In further embodiments, the germicidal lamp 304 is further configured to provide sanitization light to the cavity 308, the removable tray 324, and the dental appliances 204 supported by the removable tray 324. The germicidal lamp 304 may be any form of a lamp configured to reduce the amount of bacteria in the cavity 308, such as an incandescent lamp, a compact fluorescent lamp, a high-intensity discharge (HID) lamp, or a ultra-violet lamp. In some embodiments, the germicidal lamp 304 is a ultra-violet lamp operating at a wavelength between 200 and 300 nanometers. In further embodiments, the germicidal lamp 304 is a ultra-violet lamp operating at a wavelength of 253.7 nanometers. In some embodiments, the germicidal lamp 304 uses at least three watts of power, or more. The germicidal lamp 304 may be coupled via a wired connection to a power input 508 to receive power. In some embodiments, the germicidal lamp 304 is couple via a wired connection to a controller to receive power. The germicidal lamp 304 may include both a lightbulb and a circuit configured to power the lightbulb and control power to the lightbulb. The germicidal lamp 304 may be configured to ventilate excess heat outside of the cleaning device 100, direct the light to the shine primarily inside the cavity 308, change the wavelength of the light, alternate the wavelength of the light, etc.

The germicidal lamp 304 may be fixedly coupled to the inside of the cover 108, such that the germicidal lamp 304 moves with the cover 108. Fixedly coupling lamp 304 to the inside of the cover 108 protects the germicidal lamp 304 from coming into contact with the fluid 604. If the germicidal lamp 304 was located within the cavity 308 of the body 104, the germicidal lamp 304 would require a pressure sealed container to keep fluid 604 from entering the electrical circuit of the germicidal lamp 304. As lamps require power, contact between a conducting fluid such as water is dangerous and can result in damage to the germicidal lamp 304, or electric shock to a user of the cleaning device 100. By fixedly coupling germicidal lamp 304 to cover 108, the cost of the cleaning device 100 is reduced as the circuit of the germicidal lamp 304 is not required to be further protected from the fluid 604. As the holes 120 are also located in the cover 108, the light naturally reaches more of dental appliance 204 than if the holes 120 or the germicidal lamp 304 were not included in the cover 108. In some embodiments, the holes 120 are further located on opposite sides of the germicidal lamp 304 and angled to provide an opening that naturally guides the dental appliances 204 to the center of the cavity 308. Since the germicidal lamp 304 is approximately located at the center of underside of the cover 108, the most light shines to the center of the cavity 308. This causes the dental appliances 204 to receive the most sanitizing light, eliminating more bacteria than other configurations, shortening cleaning times, and providing a more thorough cleaning of the dental appliances 204. In further embodiments, the germicidal lamp 304 is configured to provide sanitizing light to the portion of the dental appliances 204 that are received through holes 120. As the light reaches the portion of the dental appliances 204 as soon as they enter the cavity 308, the dental appliances 204 receive a greater amount of unobstructed sanitizing light than if the germicidal lamp 304 did not reach the portion of the dental appliances 204 received through the holes 120, and thereby provides a more throughout cleaning of the dental appliances 204.

Because the germicidal lamp 304 is coupled to the cover 108, the light emitted from the germicidal lamp 304 may pierce the cover 108 and reach a user. To protect the user from direct light exposure, the cover 108, may be constructed of a material such as dark colored polymers that are designed to absorb light while allowing the user to see inside the cover 108. This shields the user from direct exposure to strong light rays, while allowing the user to see inside the cavity 308.

Referring to FIG. 5, cleaning device 100 is shown to include a power supply circuit 504. Power supply circuit 504 may be coupled via wired connection to the power input 508 and configured to provide power to the power input 508. In some embodiments, the power supply circuit 504 receives alternating current (AC) power from an external power supply and provides the AC power to the power input 508. In some embodiments, the power supply circuit 504 receives AC power from an external power supply, converts it to direct current (DC) power, and then provides DC power to the power input 508. In some embodiments, the power is received from an external power supply at 100-240 volts AC, the power is converted to 12 volt DC power, and then provided to the power input 508 at 12 volt DC power. In some embodiments, the power supply provides power to the power input 508 in a range of 14 to 30 watts, 16 to 28 watts, 18 to 26 watts, or 20 to 24 watts. In some embodiments, the power supply provides power to the power input 508 at 18 watts, 20 watts, or 26 watts.

Referring back to FIG. 4, a block diagram of a cleaning device 400 is shown, according to some embodiments. The cleaning device 400 includes body 404 and cover 408, which may be identical or substantially similar to body 104 and cover 108. Cover 408 may be pivotably coupled to body 404 and configured to selectively move between an open position and a closed position.

Cleaning device 400 includes a vibration mechanism 420. Vibration mechanism 420 may be any kind of vibration mechanism configured to vibrate the body 104 and the contents thereof. The vibration mechanism 420 can include both electric motor vibration generators and piezoelectric vibration generators. Electric motor vibration generators often operate as a small electric motor in which one or more weights have been affixed to its rotor. This causes the rotor to rotate in a dynamically unbalanced state and produce a vibration. Various electric motor vibration generators include coin vibration motors, linear resonant actuators, cylinder coreless motors, and surface mounted solderable vibration motors. A piezoelectric vibration generator operates using a piezoelectric crystal. To produce vibration, a direct current is applied across the piezoelectric crystal. Once electrically polarized, the crystal deforms axially in the direction of the polarization. If the electrical current is halted and then reverse biased, the crystal returns first back to its null position and proceeds to deform to the same magnitude in the opposite direction along a single linear axis. If the current is repeatedly applied and then reversed, the crystal, and hence the piezoelectric element, will oscillate back and forth along a single axis at the frequency of the reversing applied current producing a vibration. In some embodiments, the vibration mechanism 420 is configured to vibrate the body and the contents thereof at a frequency between 30,000 and 50,000 Hz. In some embodiments, the vibration mechanism 420 is configured to the body and the contents thereof at a frequency of 42,000 Hz.

The vibration mechanism 420 is shown to be included in the body 404. In some embodiments, the vibration mechanism 420 may be located directly under the cavity 416, so as to impart the most vibrational force to the contents of cavity 416. In some embodiments, the vibration mechanism 420 may be located in a variety of other places including outside of the body 408. In an embodiment where the vibration mechanism 420 is located outside of the body 408, it may be fixedly coupled to the body and configured to vibrate the body 408 through the coupling configuration.

In some embodiments, the vibration mechanism 420 is coupled to a controller 424 via wired or wireless communication. The vibration mechanism 424 may receive power (AC or DC) from the controller 424. When the vibration mechanism 420 receives power from the controller 424 it may activate and vibrate the body. When the vibration mechanism 420 stops receiving power from controller 424, it may deactivate and stop vibrating the body. The electric power received from the controller 424 may be either AC or DC power. In some embodiments, the vibration mechanism 420 receives 12 volts DC power from the controller 424. In other embodiments, the vibration mechanism 420 receives the power from the power supply 428.

The cleaning device 400 includes a controller 424. Controller 424 may be any sort of controller such as an independent control circuit, a microcontroller, or a small computing device dedicated to controlling the cleaning device 400. The controller 424 may be coupled via wired or wireless connections to the germicidal lamp 412, the vibration mechanism 420, the power input 428, and the push button 432. The controller may be configured to receive a signal indicating the push button 432 was pressed from the push button 432, receive power from the power input 428, provide the germicidal lamp 412 with power and provide the vibration mechanism 420 with power. In some embodiments, the controller 424 is configured to activate (e.g., power) the germicidal lamp 412 and the vibration mechanism 424 the first time a signal is received from push button 432, deactivate (e.g., unpower) the germicidal lamp 412 and activate the vibration mechanism 424 the second time a signal is received from push button 432, activate the germicidal lamp 412 and deactivate the vibration mechanism 420 the third time a signal is received from push button 432, and deactivate the germicidal lamp 412 and the vibration mechanism 420 the fourth time a signal is received from push button 432. In some embodiments, the controller 424 is configured to deactivate the germicidal lamp 412 and the vibration mechanism 420 if a predetermined time period elapses (e.g., three minutes, four minutes, five minutes, etc.) between signals being received from the push button 432. In some embodiments, the controller 424 is configured to restart the signal count if both the germicidal lamp 412 and the vibration mechanism 420 are deactivated.

Cleaning device 400 may further include a power input 428. Power input 428 may be identical or substantially the same as power input 508, with reference to FIG. 5. Power input 428 may be configured to receive DC power. The power input 428 may be coupled to the controller 424 via wire and may be further configured to supply DC power to controller 424. In some embodiments, the power input 428 is configured to receive 12 volts of DC power and supply 12 volts of DC power to the controller 424. In some embodiments, the power input 424 is simply a wired connection to an exterior power supply. In some embodiments, the power input 424 is a high voltage protection circuit that protects the controller from high voltage (e.g., greater than 5 volts) power. In some embodiments, the power input 428 receives power in a range of 14 to 30 watts, 16 to 28 watts, 18 to 26 watts, or 20 to 24 watts. In some embodiments, the power input 428 receives power at 18 watts, 20 watts, or 26 watts.

Figure 8:
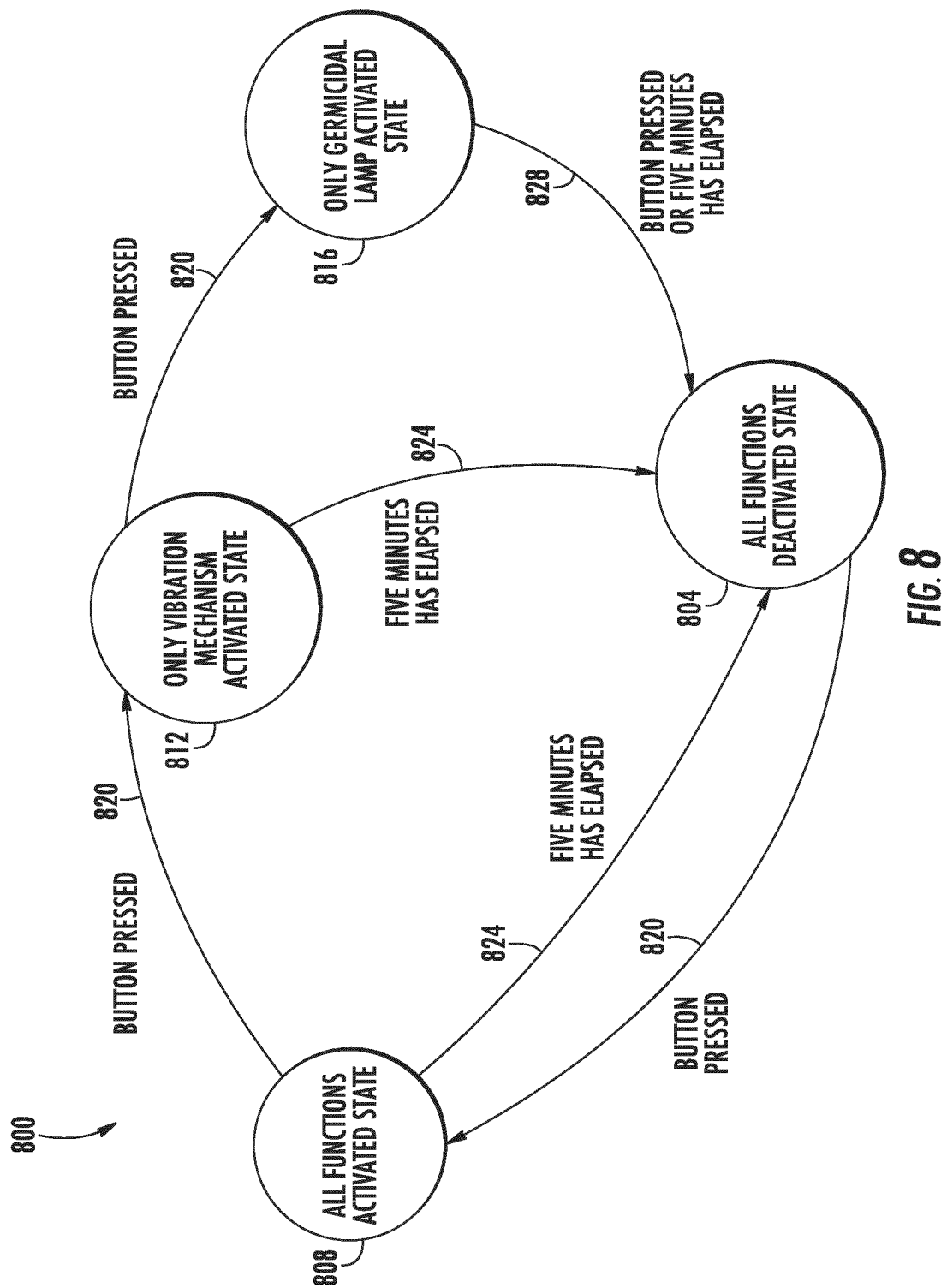
FIG. 8 is a diagram illustrating the state transitions and transition conditions experienced by the cleaning device during operation, according to some embodiments.

Turning now to FIG. 8, a diagram 800 illustrating the state transitions and transition conditions experienced by the cleaning device 400 during operation are shown, according to some embodiments. In some embodiments, the logic of state transition diagram 800 may be implemented by a controller such as controller 424 depicted in FIG. 4. For the purpose of simplicity, state transition diagram 800 will be described exclusively with reference to cleaning device 400, germicidal lamp 412, vibration mechanism 420, push button 432, and controller 424 of FIG. 4.

FIG. 8 depicts a state transition diagram 800 including logic configured to operate the cleaning device 400. As shown, state transition diagram 800 includes an all functions deactivated state 804, an all functions activated state 808, an only vibration mechanism activated state 812, and an only germicidal lamp activated state 816. The names of the states are self-descriptive but each state will be explained. The all functions deactivated state 804 is the state in which both the germicidal lamp 412 and the vibration mechanism 420 are deactivated. The all functions activated state 808 is the state in which both the germicidal lamp 412 and the vibration mechanism 420 are activated. The only vibration mechanism activated state 812 is the state in which the germicidal lamp 412 is deactivated and the vibration mechanism 420 is activated. The only germicidal lamp activated state 816 is the state in which the germicidal lamp 412 is activated and the vibration mechanism 420 is deactivated. The activation and deactivation of each mechanism is performed by the controller 424.

Under normal conditions, the cleaning device 400 may remain in the all functions deactivated state 804. If the controller 424 receives a signal from push button 432, condition 820 is satisfied and cleaning device 400 transitions from the all functions deactivated state 804 to the all functions activated state 808. The cleaning device 400 may remain in the all functions activated state 808 for up to a predetermined time period (e.g., five minutes). If the predetermined time period expires, condition 824 is satisfied and cleaning device 400 transitions from the all functions activated state 808 to the all functions deactivated state 804. If before condition 824 is satisfied the controller 424 receives a signal from push button 432, condition 820 is satisfied and the cleaning device 400 transitions to the only vibration mechanism activated state 812. The cleaning device may remain in the only vibration mechanism activated state 812 for up to a predetermined time period (e.g., five minutes). If the predetermined time period expires, condition 824 is satisfied and cleaning device 400 transitions from only vibration mechanism activated state 812 to all functions deactivated state 804. If before condition 824 is satisfied the controller 424 receives a signal from push button 432, condition 820 is satisfied and the cleaning device 400 transitions to the only germinated lamp activated state 816. Once in the only germinated lamp activated state 816, the cleaning device 400 can only transition to the all functions deactivated state 804. The cleaning device 400 will transition to the all functions deactivated state 804 if the controller 424 receives a signal from push button 432 or the predetermined time period expires, thereby satisfying condition 828.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the figures. It should be noted that the orientation of various elements may differ according to other exemplary embodiments, and that such variations are intended to be encompassed by the present disclosure.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It should be appreciated that other elements of the various embodiments may be incorporated or utilized with any of the other embodiments disclosed herein.

What is claimed is:

1. A cleaning device comprising:
a body including a cavity, the cavity configured to receive a liquid, the cavity sized to contain at least one dental appliance;
a cover coupled to the body and configured to selectively move between an open position and a closed position, the cover including two holes, each hole having an outer boundary defined by the cover and a portion of the body; and
a germicidal lamp coupled to the cover and moveable therewith, the germicidal lamp configured to provide a sanitizing light to the at least one dental appliance contained within the cavity;
wherein the cover comprises a polymer structured to absorb sanitizing light from the germicidal lamp; and
wherein the two holes are located on opposite sides and forward of the germicidal lamp such that an axis between a center point of each of the two holes is offset from the germicidal lamp, the two holes being angled toward a center of the cavity.

2. The cleaning device of claim 1, wherein the at least one dental appliance is an oral cleaning apparatus.

3. The cleaning device of claim 1, wherein the at least one dental appliance comprises a first dental appliance and a second dental appliance, the first dental appliance being a dental aligner and the second dental appliance being a toothbrush.

4. The cleaning device of claim 1, further comprising a vibration mechanism configured to vibrate the body at a frequency between 30,000 and 50,000 Hz.

5. The cleaning device of claim 1, wherein the germicidal lamp is located on an underside of the cover.

6. The cleaning device of claim 5, wherein the sanitizing light is an ultraviolet light with a wavelength between 300 and 400 nanometers.

7. The cleaning device of claim 1, wherein the cover is pivotably coupled to the body.

8. The cleaning device of claim 1, wherein the body includes silver located in a position within the body to interface with and clean at least a portion of the at least one dental appliance.

9. A cleaning device comprising:
a body including a cavity, the cavity configured to receive a liquid, the cavity sized to contain a first dental appliance and a second dental appliance;
a cover coupled to the body and configured to selectively move between an open position and a closed position, the cover including two holes opposite one another, each hole having an outer boundary defined by the cover and a portion of the body; and
a germicidal lamp configured to provide a sanitizing light to the first dental appliance and a first portion of the second dental appliance positioned within the cavity;
wherein the cover comprises a polymer structured to absorb sanitizing light from the germicidal lamp; and
wherein the two holes are located on opposite sides and forward of the germicidal lamp such that an axis between a center point of each of the two holes is offset from the germicidal lamp, the two holes being angled toward a center of the cavity.

10. The cleaning device of claim 9, wherein the first dental appliance is a dental aligner, and the second dental appliance is an oral cleaning device.

11. The cleaning device of claim 9, further comprising a vibration mechanism configured to vibrate at a frequency between 30,000 and 50,000 Hz.

12. The cleaning device of claim 9, wherein the cleaning device further includes a removable tray configured to support the first dental appliance and the first portion of the second dental appliance, and wherein the germicidal lamp is further configured to provide the sanitizing light to the first dental appliance and the first portion of the second dental appliance supported by the removable tray.

13. The cleaning device of claim 9, wherein each hole is shaped to retain the second dental appliance such that the first portion of the second dental appliance is angled toward the center of the cavity and a second portion of the second dental appliance is positioned in an area external to the cavity and the cover.

14. The cleaning device of claim 9, wherein a first hole of the two holes is shaped to retain the second dental appliance such that the first portion of the second dental appliance is angled toward the center of the cavity, and wherein a second hole of the two holes is shaped to retain a third dental appliance such that a first portion of the third dental appliance is angled toward the center.

15. The cleaning device of claim 9, wherein the sanitizing light is an ultraviolet light with a wavelength between 300 and 400 nanometers.

16. A cleaning device comprising:
a body including a cavity, the cavity configured to receive a liquid and a plurality of dental appliances;
a cover coupled to the body and configured to selectively move between an open position and a closed position, the cover including two rounded cut-outs opposite one another, each rounded cut-out angled toward a center of the cavity and forming an arch-shaped opening defined by the rounded cut-out and the body when the cover is in the closed position such that each opening is shaped to retain at least a portion of at least one dental appliance of the plurality of dental appliances, the portion of the at least one dental appliance of the plurality of dental appliances disposed to be angled toward the center of the cavity;
a germicidal lamp coupled to an underside of the cover and moveable therewith, the germicidal lamp configured to provide a sanitizing light to the portion of the at least one dental appliance the plurality of dental appliances;
wherein the two rounded cut-outs are located on opposite sides of the germicidal lamp forward of the germicidal lamp such that an axis between a center point of each of the two rounded cut-outs is offset from the germicidal lamp, the two rounded cut-outs being angled toward the center of the cavity.

17. The cleaning device of claim 16, further comprising a removable tray configured to support the at least one dental appliance, wherein the removable tray comprises at least one of a handle or a plurality of small holes configured to enable fluid to permeate the removable tray.

* * * * *